United States Patent [19]

Bigg et al.

[11] Patent Number: 4,598,086
[45] Date of Patent: Jul. 1, 1986

[54] α2 ANTAGONISTIC 2-(4,5-DIHYDRO-2-1H-IMIDAZOLYL)-2,3-DIHYDRO-1H-INDOLES

[76] Inventors: Dennis Bigg, 5, Parc de Diane, 78350 Jouy en Josas; Jacques Menin, Cité Balzac D 114 - 118, rue Balzac, 94400 Vitry sur Seine, both of France

[21] Appl. No.: 639,323

[22] Filed: Aug. 10, 1984

[30] Foreign Application Priority Data

| Aug. 11, 1983 | [FR] | France | 83 13198 |
| Oct. 17, 1983 | [FR] | France | 83 16473 |
| Nov. 15, 1983 | [FR] | France | 83 18121 |
| Feb. 9, 1984 | [FR] | France | 84 01998 |

[51] Int. Cl.$^4$ .................. A61K 31/415; C07D 403/04; C07D 405/14
[52] U.S. Cl. ..................... 514/402; 548/348
[58] Field of Search ................... 548/348; 424/273 R; 514/402

[56] References Cited

U.S. PATENT DOCUMENTS

| 4,280,327 | 6/1980 | Yonan | 548/348 |
| 4,315,019 | 2/1982 | Malen et al. | 548/348 |
| 4,328,234 | 5/1982 | Thorogood | 548/348 |
| 4,378,357 | 3/1983 | Miller et al. | 548/348 |
| 4,391,814 | 7/1983 | Vorbruggen | 548/348 |
| 4,411,908 | 10/1983 | Chapleo et al. | 548/348 |

OTHER PUBLICATIONS

Burger, "Rational Approaches to Drug Structure", J. Chem. Ed., 33, No. 8., p. 362–372, 1956.
Morrison and Boyd, "Organic Chemistry", 4th Ed., 1983, p. 902.
Barton, "Protection of N–H Bonds and NR$_3$", Protective Groups in Organic Chemistry, (Ed. Mcomie, 1976), pp. 62–63.

Primary Examiner—Richard A. Schwartz
Assistant Examiner—Kurt G. Briscoe

[57] ABSTRACT

Indole derivatives, in the form of racemates or optically active isomers, of the formula (I)

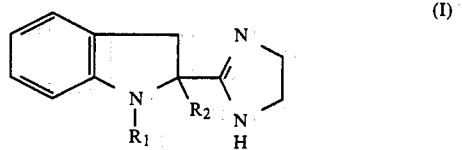

in which $R_1$ is a hydrogen atom, a linear or branched $(C_{1-6})$ alkyl group, a $(C_{3-6})$ cycloalkyl-$(C_{1-4})$ alkyl group, a $(C_{2-6})$ alkenyl group, the naphthylmethyl group, the phenethyl group or a benzyl group optionally substituted by one or more halogen atom or methyl, methoxyl or methylenedioxy group and $R_2$ is H or a $(C_{1-4})$ alkyl or allyl group, and their pharmaceutically acceptable salts; are $\alpha_2$-antagonists and useful for the treatment of depression, hypotension, post-operative paralytic ileum, asthma and obesity.

2 Claims, No Drawings

α₂ ANTAGONISTIC 2-(4,5-DIHYDRO-2-1H-IMIDAZOLYL)-2,3-DIHYDRO-1H-INDOLES

The present invention relates to indole derivatives, their preparation and their application in therapy.

The indole derivatives of the invention are of the formula (I)

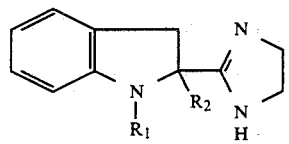

in which $R_1$ is a hydrogen atom, a linear or branched ($C_{1-6}$)alkyl group, a ($C_{3-6}$)cycloalkyl-($C_{1-4}$)alkyl group, a ($C_{2-6}$)alkenyl group, the naphthylmethyl group, the phenethyl group or a benzyl group optionally substituted by one or more halogen atom or methyl, methoxyl or methylenedioxy group and $R_2$ is H or a ($C_{1-4}$)alkyl or allyl group, and their pharmaceutically acceptable salts.

The indole derivatives of the invention can exist in the form of racemates or enantiomers.

Preferably $R_1$ is a benzyl group optionally substituted by a halogen atom or a methyl or methylenedioxy group, the allyl group or a ($C_{1-4}$)alkyl group and $R_2$ is H.

The compounds of the invention in which $R_1$ is other than a hydrogen atom may be prepared according to the following reaction scheme:

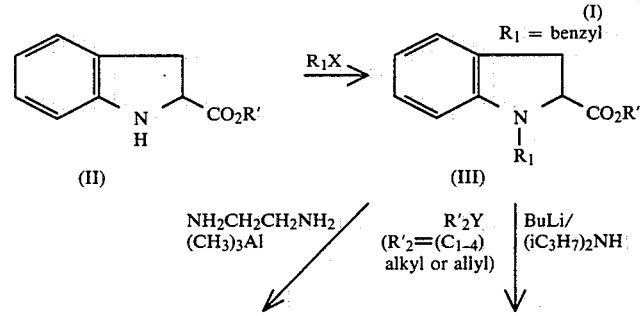

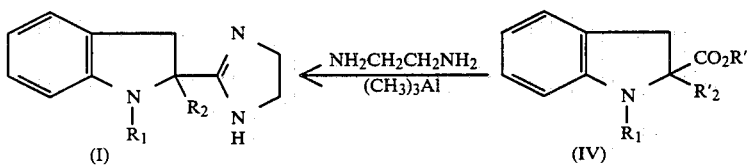

in which R' is a ($C_{1-4}$)alkyl group, in particular ethyl, and X and Y are labile groups, in particular iodine or bromine atoms.

The compounds of the invention in which $R_1$ is a hydrogen atom may be prepared according to either of the two Schemes 1 and 2 below.

Scheme 1

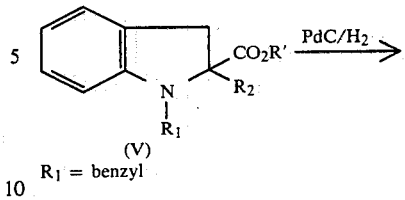

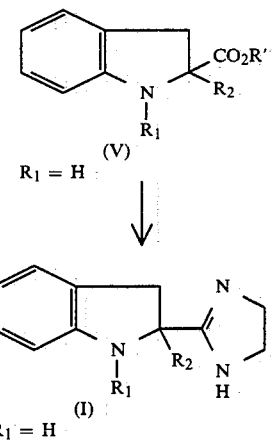

Scheme 2

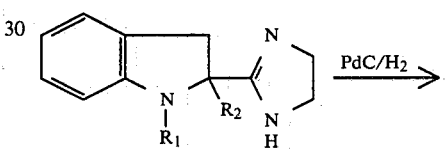

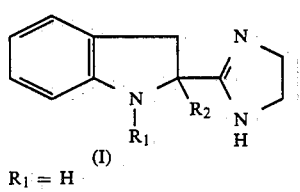

The starting ethyl ester (R'=ethyl in formula II) is prepared according to the method described by E. J. Corey et al., J. Am. Chem. Soc., 92, 2476 (1970).

The reaction between the starting ester (II), for example ethyl 2,3-dihydro-2-1H-indolecarboxylate, and the compound $R_1X$ can be carried out in a solvent such as acetone, methyl ethyl ketone or dimethylformamide, at room temperature or at a higher temperature, in the presence of a base, such as potassium carbonate. The reaction may be catalysed, for example by addition of sodium iodide.

The optional alkylation or alkenylation of the ester (III) prepared in this way is carried out by the reaction of a halide $R'_2Y$ with the lithiated derivative prepared in situ by means of lithium diisopropylamide (butyllithium + diisopropylamine).

The formation of the indole derivative (I) from the ester (III) or the ester (IV) is carried out with ethylenediamine in the presence of trimethylaluminium.

The debenzylation of the compound (V) or of the compound (I) in which $R_1$ is benzyl, to obtain a compound (V) or compound (I) respectively in which $R_1$ is a hydrogen atom, is carried out with the aid of hydrogen under pressure in the presence of palladium on charcoal.

The following examples and the Table illustrate the invention. The structure of the compounds obtained according to the invention was confirmed by analysis and IR and NMR spectra.

EXAMPLE 1

2-(4,5-dihydro-2-1H-imidazolyl)-2,3-dihydro-1-methyl-1H-indole

The reaction is conducted under nitrogen or argon. 2.28 ml (0.034 mole) of ethylenediamine dissolved in 6 ml of toluene are added to a cold solution of trimethylaluminium (14.2 ml at 25% strength in hexane; 0.034 mole) in 22 ml of toluene.

The reaction mixture is heated to 50°-60° C. and 4.4 g (0.021 mole) of 2,3-dihydro-2-ethoxycarbonyl-1-methyl-1H-indole in 6.3 ml of toluene are added.

The reaction mixture is heated to reflux temperature and approximately 30 ml of solvent are removed by means of a Dean-Stark apparatus, reflux temperature is maintained for 12 hours, the reaction mixture is cooled and 14 ml of water are added, and the precipitate is filtered off and washed with ethyl acetate.

The organic phases are combined and washed once with water saturated with sodium chloride. The organic phase is dried over $MgSO_4$, filtered and evaporated.

The base obtained is dissolved in 50 ml of ethanol and treated with a solution of fumaric acid in ethanol. The salt obtained is recrystallised from ethanol.

M.p. = 178°-180° C.

EXAMPLE 2

2-(4,5-dihydro-2-1H-imidazolyl)-2,3-dihydro-1-benzyl-1H-indole

The reaction is conducted under nitrogen or argon. 1.8 ml (0.027 mole) of ethylenediamine dissolved in 5 ml of toluene are added to a cold solution of trimethylaluminium (11.4 ml at 25% strength in hexane; 0.027 mole) in 18 ml of toluene.

The reaction mixture is heated to 50°-60° C. and 4.8 g (0.017 mole) of 2,3-dihydro-2-ethoxycarbonyl-1-benzyl-1H-indole in toluene are added.

The reaction mixture is heated to reflux temperature and approximately 15 ml of solvent are removed by means of a Dean-Stark apparatus, reflux temperature is maintained for 2 h 30 min, the reaction mixture is cooled and 11 ml of water are added, the precipitate is filtered off and washed with ethyl acetate.

The organic phases are combined and washed once with water saturated with sodium chloride. The organic phase is dried over $MgSO_4$, filtered and evaporated.

The base obtained is dissolved in 50 ml of ethanol and treated with a solution of fumaric acid in ethanol. The salt obtained is recrystallised from ethanol.

M.p. = 172°-173.5° C.

EXAMPLE 3

2-(4,5-dihydro-2-1H-imidazolyl)-1-(4-methoxybenzyl)-2,3-dihydro-1H-indole 1. 5.16 g (0.027 mole) of ethyl 2,3-dihydro-2-1H-indolecarboxylate and 6 g (0.043 mole) of $K_2CO_3$ in 50 ml of DMF are introduced, under argon.

4.65 g (0.0297 mole) of 4-methoxybenzyl chloride and 4 g (0.027 mole) of NaI are then added.

The reaction mixture is stirred for 4 hours at room temperature, and is then poured into iced water and extracted with ether. The ether solution is washed with water, then with dilute $NaHSO_3$, and then with water. It is dried, filtered and concentrated. Crude ethyl 1-(4-methoxybenzyl)-2,3-dihydro-2-1H-indolecarboxylate is obtained and used as such in the second stage.

2. The reaction is conducted under argon. 2.55 ml (0.038 mole) of ethylenediamine dissolved in 10 ml of toluene are added to a cold solution of trimethylaluminium (16.15 ml at 25% strength in hexane; 0.038 mole) in 28 ml of toluene.

The reaction mixture is heated to 50°-60° C. and 7.5 g (0.024 mole) of the ester obtained earlier, dissolved in 27 ml of toluene, are added.

The reaction mixture is heated to reflux temperature and approximately 20 ml of solvent are removed by means of a Dean-Stark apparatus; reflux temperature is maintained for 12 hours; the reaction mixture is cooled and 16 ml of water are added, the precipitate is filtered off and washed with dichloromethane.

The organic phases are combined and washed once with water. The organic phase is dried over $MgSO_4$, filtered and evaporated. The product is obtained in the form of an oil which is dissolved in 150 ml of ethanol and treated with a solution of fumaric acid (2.1 g) in ethanol (100 ml).

The product crystallises slowly. It is filtered off and crystallised from ethanol.

M.p. = 154°-156° C.

EXAMPLE 4

2-(4,5-dihydro-2-1H-imidazolyl)-1-n-butyl-2,3-dihydro-1H-indole 1. 5.16 g (0.027 mole) of ethyl 2,3-dihydro-2-1H-indolecarboxylate and 6.0 g (0.043 mole) of $K_2CO_3$ in 50 ml of DMF are placed in a round flask, under argon.

22.0 g (0.12 mole) of iodobutane are then added and the mixture is heated to 60° C. for 9 hours with continuous stirring. It is then poured into a mixture of water and ice, extracted with ether, and the organic phase is washed, dried and concentrated. A yellow oil is obtained which, when purified by chromatography and then by distillation, has a boiling point of 120° C. at a pressure of 0.7 Pa (0.005 mm Hg).

2. A solution of 1.33 g (0.0221 mole) of ethylenediamine in 5 ml of toluene is added, at 0°-5° C., to a solution of 1.55 g (0.0214 mole) of trimethylaluminium in 15 ml of toluene. The mixture is heated to 50° C., and 3.4 g (0.014 mole) of ethyl 1-n-butyl-2,3-dihydro-1H-indolecarboxylate dissolved in 20 ml of toluene are added and the whole is refluxed for 24 hours.

The mixture is then hydrolysed with 20 ml of water, the precipitate is separated off by filtration and washed with ethyl acetate. The organic phases are combined, washed with water, dried and concentrated. An oil is obtained which crystallises in petroleum ether, forming a white solid.

This white solid is taken up in ethanol and treated with an equivalent of fumaric acid. The mixture is concentrated, triturated with acetone, and the solid obtained is recrystallised from a mixture of acetone and isopropyl alcohol.

MP=111.5°-113° C.

EXAMPLE 5

1,2-dimethyl-2-(4,5 dihydro-2-1H-imidazolyl)-2,3-dihydro-1H-indole 1. 5 ml (0.036 mole) of diisopropylamine in 30 ml of tetrahydrofuran and 22.5 ml (0.036 mole) of butyllithium (1.6M in hexane) are placed in a round flask, under argon and at −78° C.

The mixture is stirred for one hour at −78° C., then 6.2 g (0.030 mole) of ethyl 1-methyl-2,3-dihydro-2-1H-indole-carboxylate dissolved in 20 ml of tetrahydrofuran are added and stirring is continued for an hour at −78° C. Finally, 21.3 g, i.e. 9.3 ml (0.150 mole) of iodomethane are added, stirring is continued for another hour at −78° C. and the mixture is allowed to warm up to room temperature. It is then poured onto a mixture of water and ice, extracted with ether, and the organic phase is washed with water, dried and concentrated. An orange oil is obtained which is purified by chromatography on silica by elution with a 98/2 mixture of cyclohexane and ethyl acetate.

After being distilled, the oil obtained has a boiling point of 110°-115° C. at 0.67 Pa (0.005 mm Hg).

2. To a solution of 1.34 g (0.0185 mole) of trimethylaluminium (7.75 ml of a solution at 25% strength in hexane) in 15 ml of toluene is added, under argon and between 0° and 5° C., dropwise and over a period of 30 minutes, a solution of 1.14 g, i.e. 1.3 ml (0.019 mole) of ethylene diamine in 5 ml of toluene, while the temperature is maintained between 0° and 5° C. The mixture is then heated to 50° C. and 2.6 g (0.012 mole) of the oil obtained previously, dissolved in 20 ml of toluene are added dropwise. When the addition is completed, the mixture is heated to 80°-90° C., the hexane is distilled off and the mixture is refluxed for 18 hours while the reaction is followed by thin layer chromatography. A clear yellow solution is left at the end; this is hydrolysed with 20 ml of water, while being cooled in an ice bath. The whitish solution obtained is filtered, extracted with methylene chloride and the extract is washed, dried and concentrated. In this way an orange oil is obtained which is taken up in ether and this solution is poured into a solution of benzoic acid in ether. A white solid precipitates and separated off and recrystallised from ethyl acetate. The benzoate melts between 118.5° and 120° C.

EXAMPLE 6

2-(4,5-dihydro-2-1H-imidazolyl)-2-n-propyl-2,3-dihydro-1H-indole

This compound was prepared according to the two reaction schemes 1 and 2.

1. Scheme 1

1.1. 9.75 g (0.03 mole) of 2,3-dihydro-2-ethoxycarbonyl-2-n-propyl-1-benzyl-1H-indole in 100 ml of acetic acid and 0.5 g of palladium at a concentration of 10% on charcoal are placed in a 500 ml Parr apparatus. Hydrogen is introduced under a pressure of 0.4 Mpa and stirring is continued for 8 hours at an ambient temperature. The reaction mixture is filtered, concentrated, taken up with ether, washed with an aqueous solution of NaHCO$_3$ and then with water to pH 6-7. It is dried over MgSO$_4$, filtered, the reaction mixture is concentrated and distilled in a ball oven.

2,3-Dihydro-2-ethoxycarbonyl-2-n-propyl-1H-indole is obtained as a yellow oil. 1.2 70 ml of toluene and 34.4 ml (0.082 mole) of a 25% solution of trimethylaluminium in hexane are introduced in succession into a 250 ml Keller flask fitted with magnetic stirring, a condenser, an argon inlet and a dropping funnel.

The reaction mixture is cooled with an ice bath and a solution of 5.5 ml (0.082 mole) of ethylenediamine in 25 ml of toluene is added.

The mixture is heated to approximately 50°-60° C. and a solution of 60 g (0.0257 mole) of the compound obtained earlier under 1.1., in 30 ml of toluene, is added. The mixture is heated for 2 h at the reflux temperature. It is cooled to about −10° C. and hydrolysed with 35 ml of water. It is filtered, and rinsed with ethyl acetate and then with CH$_2$C$_2$. The organic phases are combined and washed twice with water. They are dried over NgSO$_4$, filtered and concentrated.

The oil obtained is taken up in 100 ml of orthodichlorobenzene. 1 spatula end of p-toluenesulphonic acid is added and the material is heated to reflux temperature under argon for 18 h, with a Dean-Stark head fitted to the flask.

The mixture is taken up in methylene chloride, washed twice with water, dried over MgSO$_4$, filtered and concentrated, after treatment with animal charcoal, the base obtained is converted to a fumarate by reacting 2.7 g (0.0231 mole) of fumaric acid dissolved in 135 ml of ethanol with 5.8 g (0.0257 mole) of base, dissolved in 50 ml of ethanol.

The material is concentrated, and taken up in acetone. The product crystallises. It is filtered off and re-crystallised from isopropanol and then from ethanol. The product melts at 167°-169° C.

2. Scheme 2

4.4 g (0.0137 mole) of 2-(4,5-dihydro-2-1H-imidazolyl)-2-n-propyl-1-benzyl-2,3-dihydro-1H-indole dissolved in 100 ml of acetic acid are introduced into a 500 ml Parr apparatus. 0.44 g of 10% palladium on charcoal is added and then hydrogen is introduced under a pressure of 0.4 Mpa. The mixture is heated for 8 hours at 80°-90° C.

The mixture is filtered, concentrated and taken up with water. The mixture is made alkaline with caustic soda solution and extracted with methylene chloride. The organic phase is washed 3 times with water, dried over MgSO$_4$, filtered and concentrated.

The base is converted to a fumarate by reacting 3.2 g (0.0137 mole) of base dissolved in 50 ml of ethanol with 1.54 g (0.0132 mole) of fumaric acid dissolved in 75 ml of ethanol. The material is concentrated, taken up in isopropanol, filtered off and the compound is re-crystallised from ethanol. MP=167°-169° C.

The compounds of the invention which have been prepared by way of example, are shown in the following table.

TABLE

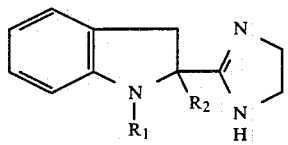

I

| Compound | $R_1$ | $R_2$ | Salt | M.p. (°C.) |
|---|---|---|---|---|
| 1 | $CH_3$ | H | fumarate | 178–180 |
| 2 | $C_6H_5CH_2$ | H | fumarate | 172–173.5 |
|   |   |   | methanesulphonate | 188–9 |
| 3 | $4\text{-}CH_3\text{—}C_6H_4CH_2$ | H | fumarate | 139–40 |
| 4 | $3\text{-}CH_3\text{—}C_6H_4CH_2$ | H | fumarate | 160–1 |
| 5 | $4\text{-}Cl\text{—}C_6H_4CH_2$ | H | fumarate | 178–80 |
| 6 | α-naphthyl-$CH_2$ | H | fumarate | 230–2 |
| 7 | $3,4\text{-}Cl_2\text{—}C_6H_3CH_2$ | H | fumarate | 127–9 |
| 8 | $4\text{-}CH_3O\text{—}C_6H_4CH_2$ | H | fumarate | 154–6 |
| 9 | $2,6\text{-}Cl_2\text{—}C_6H_3CH_2$ | H | HCl | 226–30 |
| 10 | $3,4\text{-}(OCH_2O)\text{—}C_6H_3CH_3$ | H | fumarate | 178–80 |
| 11 | $2\text{-}F\text{—}C_6H_4CH_2$ | H | fumarate | 150–1 |
| 12 | $4\text{-}Br\text{—}C_6H_4CH_2$ | H | fumarate | 171–5 |
| 13 | $n\text{-}C_3H_7$ | H | fumarate | 130.5–132.5 |
| 14 | $n\text{-}C_4H_9$ | H | fumarate | 111.5–113 |
| 15 | $CH_2\text{-cyclohexyl-S}$ | H | fumarate | 172.5–175 |
| 16 | $i\text{-}C_4H_9$ | H | fumarate | 163.5–164.5 |
| 17 | $CH_2CH\text{=}CH_2$ | H | fumarate | 128–130 |
| 18 | $CH_2\text{-cyclopropyl}$ | H | fumarate | 176–178 |
| 19 | $n\text{-}C_6H_{13}$ | H | fumarate | 115–117 |
| 20 | $CH_3$ | $CH_3$ | benzoate | 118.5–120 |
| 21 | $CH_3$ | $CH_2CH_3$ | fumarate | 129–130 |
| 22 | $CH_3$ | $CH_2CH_2CH_3$ | fumarate | 157–159 |
| 23 | $CH_3$ | $CH_2CH\text{=}CH_2$ | fumarate | 177–179 |
| 24 | $CH_2CH\text{=}CH_2$ | $CH_3$ | fumarate | 152–164 |
| 25 | $C_6H_5CH_2$ | $CH_2CH_3$ | fumarate | 164–166 |
| 26 | $CH_2CH\text{=}CH_2$ | $CH_2CH_2CH_3$ | fumarate | 160.5–162 |
| 27 | $C_6H_5CH_2$ | $CH_3$ | fumarate | 183–186 |
| 28 | $C_6H_5CH_2$ | $nC_3H_7$ | base | 93–95 |
| 29 | $C_6H_5CH_2CH_2$ | H | fumarate | 158–160 |
| 30 | H | $CH_3$ | fumarate | 139–140 |
| 31 | H | $C_2H_5$ | fumarate | 148.5–150 |
| 32 | H | $nC_3H_7$ | fumarate | 167–169 |

The compounds of the invention have been subjected to pharmacological trials which have demonstrated their advantage as α2-antagonists.

The compounds were studied for this purpose in the test for potential and selectivity of antagonists in respect of α2 receptors in vitro.

The determination of the pA2 value in respect of the inhibitory effects of clonidine, a well known α2-agonist was carried out on the rat vas deferens stimulated at a frequency of 0.1 Hz in the presence of 30 nM of prazosine and 1 μM of cocaine, according to the method described by G. M. Drew (European Journal of Pharmacology, 42, (1977) 123–130).

The pA2 values of the compounds of the invention lie between 6 and 10.

The compounds of the invention are powerful α2-antagonists which may be employed for the treatment of depression (either alone or in association with a product inhibiting the mechanisms of neuronal capture), the treatment of hypotension, the treatment of post-operative paralytic ileum, and the treatment of asthma and obesity.

The pharmaceutical compositions may be in a suitable form for oral, rectal or parenteral administration; for example in the form of capsules, tablets, granules, gelatine capsules of liquid solutes, syrups or drinkable suspensions and may contain suitable excipients.

The daily posology may range from 0.1 to 10 mg/kg p.o.

We claim:

1. An indole derivative, in the form of the racemate or an optically active isomer, of the formula

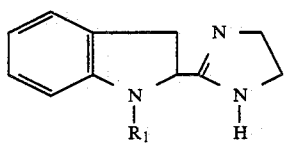

wherein $R_1$ is selected from the group consisting of methyl, n-propyl, n-butyl, isobutyl, cyclopropylmethyl, allyl, phenethyl, benzyl, 4-methylbenzyl, chlorobenzyl, fluorobenzyl, and methylenedioxybenzyl or a pharmaceutically acceptable salt thereof.

2. A pharmaceutical composition for use as an $\alpha_2$ antagonist which comprises, as active ingredient, an effective amount of at least one indole derivative or salt as claimed in claim 1 in association with a pharmaceutically acceptable excipient.

* * * * *

Notice of Adverse Decision in Interference

In Interference No. 101,846, involving Patent No. 4,598,086, D. Bigg and J. Menin, ALPHA$_2$ ANTAGONISTIC 2-(4,5-DIHYDRO-2-1H-IMIDAZOLYL)-2,3-DIHYDRO-1H-INDOLES, final judgment adverse to the patentees was rendered Aug. 31, 1989, as to claims 1 and 2.

*[Official Gazette November 21, 1989]*